(12) United States Patent
Duke et al.

(10) Patent No.: US 11,317,562 B2
(45) Date of Patent: May 3, 2022

(54) GENERATING A YIELD MAP FOR AN AGRICULTURAL FIELD USING CLASSIFICATION AND REGRESSION METHODS

(71) Applicant: Farmers Edge Inc., Winnipeg (CA)

(72) Inventors: Guy Dion Duke, Lethbridge (CA); Kevin John Grant, Lethbridge (CA)

(73) Assignee: Farmers Edge Inc., Winnipeg (CA)

( * ) Notice: Subject to any disclaimer, the term of this patent is extended or adjusted under 35 U.S.C. 154(b) by 906 days.

(21) Appl. No.: 16/126,697

(22) Filed: Sep. 10, 2018

(65) Prior Publication Data

US 2019/0075727 A1    Mar. 14, 2019

Related U.S. Application Data

(60) Provisional application No. 62/556,975, filed on Sep. 11, 2017.

(51) Int. Cl.
*G06V 20/10*    (2022.01)
*G01N 33/02*    (2006.01)
(Continued)

(52) U.S. Cl.
CPC ......... *A01D 41/1272* (2013.01); *G01N 33/02* (2013.01); *G06Q 50/02* (2013.01); *G06V 20/188* (2022.01)

(58) Field of Classification Search
None
See application file for complete search history.

(56) References Cited

U.S. PATENT DOCUMENTS 6,549,852 B2    4/2003    Hanson
6,651,005 B2    11/2003   O'Neall
(Continued)

FOREIGN PATENT DOCUMENTS

CA    2663917 C    10/2010
CA    2697608 A1    9/2011
(Continued)

OTHER PUBLICATIONS

Ping et al. ("Processing of Yield Map Data", 2005, Precision Agriculture, 6, 193-212) (Year: 2005).*
(Continued)

*Primary Examiner* — Roy Y Yi
(74) *Attorney, Agent, or Firm* — Ryan W. Dupuis; Kyle R. Satterthwaite; Ade & Company Inc.

(57) ABSTRACT

A yield model generates a yield map for an agricultural field. A measurement system generates measured indicators that are a measurement or quantification of crop yield in the agricultural field. An observation system generates observed indicators that are spatial agricultural datasets describing observed characteristics of the agricultural field. To generate the yield map, the yield model generates a field array representing the agricultural field. The yield model generates an input array and a yield array by mapping the observed indicators and measured indicators to cells of the field array, respectively. The yield model determines a yield value for each cell of the yield array not including a mapped indicator using information included in the corresponding cells of the input array. The yield model generates a yield map using the determined yield values and the yield values in the yield array.

20 Claims, 9 Drawing Sheets

(51) Int. Cl.
  *G06Q 50/02* (2012.01)
  *A01D 41/127* (2006.01)

(56) References Cited

U.S. PATENT DOCUMENTS

| | | | |
|---|---|---|---|
| 7,702,597 | B2 | 4/2010 | Singh et al. |
| 8,065,124 | B2 | 11/2011 | Xu et al. |
| 8,412,419 | B1 | 4/2013 | Seamon et al. |
| 8,917,336 | B2 | 12/2014 | Cote et al. |
| 9,037,521 | B1 * | 5/2015 | Mewes ............... A01B 79/005 706/12 |
| 9,113,118 | B2 | 8/2015 | Silverstein et al. |
| 9,131,196 | B2 | 9/2015 | Lim et al. |
| 9,131,644 | B2 | 9/2015 | Osborne |
| 9,195,891 | B2 | 11/2015 | Scharf et al. |
| 9,230,177 | B2 | 1/2016 | Dolinar et al. |
| 9,342,858 | B2 | 5/2016 | Cote et al. |
| 2005/0100220 | A1 | 5/2005 | Keaton et al. |
| 2010/0079333 | A1 | 4/2010 | Janky et al. |
| 2011/0276336 | A1 | 11/2011 | Sweely |
| 2013/0066666 | A1 | 3/2013 | Anderson et al. |
| 2013/0124239 | A1 | 5/2013 | Rosa et al. |
| 2013/0321677 | A1 | 12/2013 | Cote et al. |
| 2013/0322753 | A1 | 12/2013 | Lim et al. |
| 2014/0032271 | A1 | 1/2014 | Nordstrand |
| 2014/0358486 | A1 | 12/2014 | Osborne |
| 2014/0379228 | A1 | 12/2014 | Batcheller et al. |
| 2015/0015692 | A1 | 1/2015 | Smart |
| 2015/0116330 | A1 | 4/2015 | Chiocco et al. |
| 2015/0206255 | A1 | 7/2015 | Groeneveld |
| 2015/0327440 | A1 | 11/2015 | Dybro et al. |
| 2015/0370935 | A1 | 12/2015 | Starr |
| 2015/0371161 | A1 | 12/2015 | Mueller et al. |
| 2016/0050840 | A1 | 2/2016 | Sauder et al. |
| 2016/0055593 | A1 | 2/2016 | Groeneveld |
| 2016/0063639 | A1 | 3/2016 | Groeneveld |
| 2016/0066505 | A1 | 3/2016 | Bakke et al. |
| 2016/0071223 | A1 | 3/2016 | Rupp et al. |
| 2016/0071410 | A1 | 3/2016 | Rupp et al. |
| 2016/0073573 | A1 | 3/2016 | Ethington et al. |
| 2016/0078304 | A1 | 3/2016 | Bremer et al. |
| 2016/0078570 | A1 | 3/2016 | Ethington et al. |
| 2016/0084813 | A1 | 3/2016 | Anderson et al. |
| 2016/0084987 | A1 | 3/2016 | Dybro et al. |
| 2016/0171680 | A1 | 6/2016 | Lobell |
| 2016/0180473 | A1 | 6/2016 | Groeneveld |
| 2016/0202227 | A1 | 7/2016 | Mathur et al. |
| 2016/0232621 | A1 | 8/2016 | Ethington et al. |
| 2016/0247082 | A1 | 8/2016 | Stehling et al. |
| 2016/0290918 | A1 | 10/2016 | Xu et al. |

FOREIGN PATENT DOCUMENTS

| | | |
|---|---|---|
| EP | 2491721 B1 | 6/2016 |
| GB | 2531908 A | 5/2016 |
| WO | WO2010126783 A2 | 11/2010 |
| WO | WO 2010126783 A3 | 11/2010 |
| WO | WO 2015092800 A1 | 6/2015 |
| WO | WO 2015200489 A1 | 12/2015 |
| WO | WO 2016037105 A1 | 3/2016 |
| WO | WO 2016099723 A2 | 6/2016 |
| WO | WO 2016127094 A1 | 8/2016 |
| WO | WO2016144818 A1 | 9/2016 |
| WO | WO 2016160384 A1 | 10/2016 |
| WO | WO 2016164147 A1 | 10/2016 |

OTHER PUBLICATIONS

Sluiter, R., "Interpolation Methods for Climate Data", Intern Rapport; IR Apr. 2009, Literature review, KNMI, R&D Information and Observation Technology, De Bilt, Nov. 19, 2008, Version 1.0, 28 pages.

Hofstra, N. et al., "Comparison of Six Methods for the Interpolation of Daily, European Climate Data," American Geophysical Union, Journal of Geophysical Research, vol. 113, D21110, 2008, 19 pages.

Li, J. et al., "A Review of Spatial Interpolation Methods for Environmental Scientists," Australian Government, Record 2008/23, Geocat#68229, 2008, 154 pages.

Sudduth, K.A. et al., "Yield Editor: Software for Removing Errors from Crop Yield Maps," Agronomy Journal, Nov.-Dec. 2007, pp. 1471-1482, vol. 99.

Singer, J.W. et al., "Soybean Growth and Seed Yield Response to Tillage and Compost," Agronomy Journal, 2008, pp. 1039-1046, vol. 100, Issue 4.

Newlands, N.K. et al. "An Integrated, Probabilistic Model for Improved Seasonal Forecasting of Agricultural Crop Yield Under Environmental Uncertainty," Frontiers in Environmental Science, Jun. 5, 2014, pp. 1-21, vol. 2, No. 17.

* cited by examiner

GENERATING A YIELD MAP FOR AN AGRICULTURAL FIELD USING CLASSIFICATION AND REGRESSION METHODS

CROSS REFERENCE TO RELATED APPLICATIONS

This application claims the benefit of priority to U.S. Provisional Application No. 62/556,975, filed Sep. 11, 2017 which is incorporated herein by reference in its entirety for all purposes.

TECHNICAL FIELD OF INVENTION

This invention relates generally to generating a yield map for an agricultural field, and more specifically to using a yield model including current measurements and previous observations as indicators for the yield model.

BACKGROUND

Advances in the data technology including ubiquitous connectivity, cheap storage, and cloud-computing power have made data, including agricultural data, accessible for analysis. However, while the technology for measuring, observing, and storing agricultural data continues to improve, it is not always possible to measure a data set completely, or with perfect accuracy. In particular, agricultural data pertaining to crop yield generally includes erroneous data points.

In an ideal environment, a continuous function that allows determination of crop yield from agricultural data would generate highly accurate yield values. However, because continuous functions use agricultural data that includes erroneous data points, determination of crop yield based on that agricultural data are inaccurate. Accordingly, a method to generate a highly accurate yield values using agricultural data that can include erroneous data points would be useful.

SUMMARY OF INVENTION

A system environment includes a number of systems to facilitate a yield model generating a yield map for an agricultural field. The system environment includes a client system, a network system, a measurement system, and an observation system. A client system is operated by an operator that is a person responsible for management of the agricultural field. The client system executes a yield model that generates a yield map in the system environment.

The measurement system generates measured indicators. Measured indicators are a measurement or quantification of crop yield in the agricultural field. The observation system generates observed indicators. Observed indicators are any type of spatial agricultural datasets or observations describing observed characteristics of the agricultural field. The network system accesses observed indicators from the observation system and measured indicators from the measurement system and provides them to the client system. The yield model utilizes the measured indicators and observed indicators to generate a yield map for the agricultural field.

To generate the yield map, the yield model generates a field array representing the agricultural field. The field array includes a number of cells with each cell representing an area of the agricultural field. The yield model generates an input array by mapping the observed indicators to cells of the field array. The yield model generates a yield array by mapping the measured indicators to cells of the field array. The yield model determines a yield value for each cell of the yield array, not including a mapped indicator using information included in the corresponding cells of the input array. The yield model generates a yield map using the determined yield values and the yield values in the yield array. The yield model generates a visualization of the yield map and transmits the visualization to the operator of the client system.

The figures depict various embodiments for purposes of illustration only. One skilled in the art will readily recognize from the following discussion that alternative embodiments of the structures and methods illustrated herein may be employed without departing from the principles described herein.

DESCRIPTION OF INVENTION

I. Introduction

This method seeks to generate a yield map for an agricultural field using a yield model that leverages indicators obtained from field measurement and observation systems. A yield map is a visual representation of yield values for a number of areas of the agricultural field. Herein, a yield value is a quantification of yield for an area of the field, such as, for example, bushels harvested per acre, or dollars per acre. The yield model generates a yield map from a data structure that includes a number of data cells where each data cell represents an area of the field. The yield model populates each data cell with a yield value using machine learning algorithms that utilize the indicators obtained from the measurement and observation systems.

II. System Environment

Figure 1:
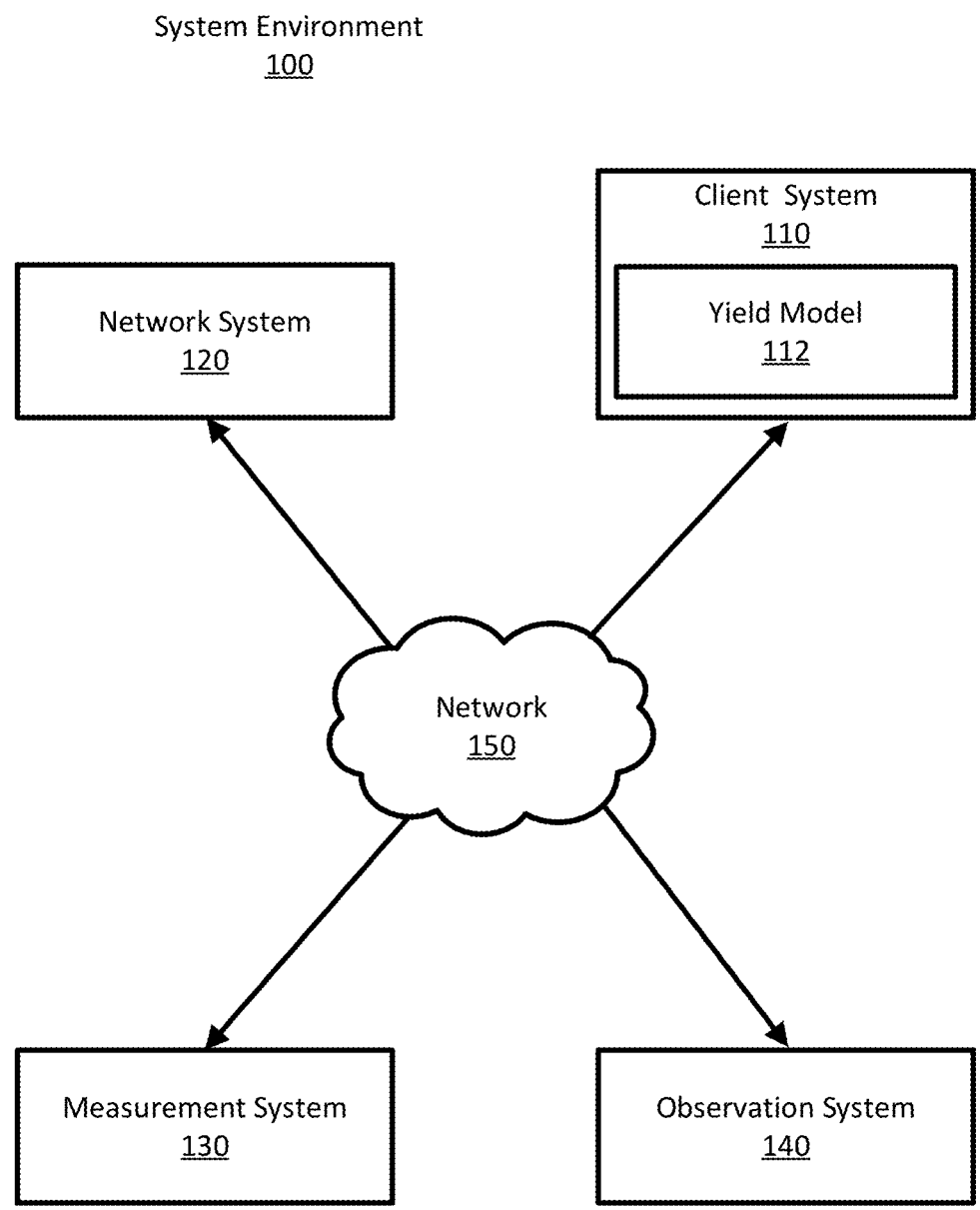
FIG. 1 is an illustration of a system environment for generating a yield map of an agricultural field using a yield model, according to one example embodiment.

FIG. 1 illustrates a system environment 100 for generating a yield map for an agricultural field. Within the system environment 100, a client system 110 generates a yield map using a yield model 112. A network system 120 accesses measured indicators and observed indicators from a measurement system 130 and an observation system 140 via a network 150, respectively. When generating a yield map for an agricultural field, a client system 110 may request measured indicators and observed indicators ("indicators" in aggregate) via the network 150 and the network system 120 may provide the indicators in response. The indicators are data used by the yield model 112 to generate a yield map. In various embodiments, the system environment 100 may include additional or fewer systems. Further, the capabilities attributed to one system within the environment may be distributed to one or more other systems within the system environment 100.

A client system 110 is any system capable of executing yield model 112 to generate a yield map for an agricultural field. The client system 110 may be a computing device, such as, for example, a personal computer. Network system 120 may also be a computing device, such as, for example, a set of servers that can operate with or as part of another system that implements network services for facilitating determining yield values. In some examples, the yield model 112 may be executed on the network system 120 rather than the client system 110. Network system 120 and client system 110 comprise any number of hardware components and/or computational logic for providing the specified functionality. That is, the systems herein can be implemented in hardware, firmware, and/or software (e.g., a hardware server comprising computational logic), other embodiments can include additional functionality, can distribute functionality between systems, can attribute functionality to more or fewer systems, can be implemented as a standalone program or as part of a network of programs, and can be loaded into memory executable by processors.

In one example, a client system 110 is operated by a user responsible for managing crop production in an agricultural field. The user of the client system 110 inputs a request for a yield map for an agricultural field into the yield model 112 and the yield model 112 generates a yield map for the agricultural field in response. Generally, the agricultural field is located at a field location and the agricultural field has a field shape and a field size. The agricultural field can include any number of sub-areas that, in aggregate, approximate the field size and field shape. In many instances, the agricultural field is managed by the user of client system 110 but could be managed by any other person. In some instances the client system 110 may be located within, or approximately adjacent to, the agricultural field. For example, the client system 110 may reside on a farming machine operating in or near the agricultural field for which a yield map is being generated.

A client system 110 is connected to a network system 120 via a network 150. The network system 120 facilitates the yield model 112 accurately determining yield values for a yield map. In various examples, the network system 120 may access measured indicators from a measurement system 130 and/or access observed indicators from an observation system 140 ("indicators" in aggregate). The network system 120 can provide the indicators to the client system 110 such that the yield model 112 can generate a yield map for an agricultural field. In some examples, the network system 120 (or the client system 110) may store any of the indicators in a datastore. Stored indicators may be accessed by yield model 112 to determine yield values for a yield map. Additionally, generated yield maps may be stored in a datastore. In some examples, the yield model 112 is executed on a network system 120 and a client system 110 accesses the yield model via the network 150.

A measurement system 130 is any system or device that can obtain and provide measured indicators to the network system 120 and client system 110 via the network 150. Measured indicators are a measurement and/or quantification of agricultural field production (e.g., crop yield). In some examples, a measurement system is a system or device capable of determining measurement indicators in real-time.

One example measured indicator is crop yield. Crop yield can be denoted in a variety of ways, from aggregate production values (e.g. bushels/acre across a field), to spatial variations (relative yield differences between two zones). Within the system environment 100, crop yield can be determined by a measurement system 130 as it travels through an agricultural field harvesting crops. A measurement system 130 determines crop yield for numerous locations in an agricultural field. Further, the measurement system 130 associates a measured indicator with the position at which it was determined. A measurement system 130 may also determine (e.g., derive, interpolate, etc.) other indicators from measured indicators, such as, for example, aggregate statistics, spatial variations, etc.

In one example, a measurement system 130 is a set of sensors on a harvester combine that measures the weight of grain being collected (e.g., at a rate of kilograms per second). The measurement system 130, combines the measured rate with other information (swath width, crop type, grain moisture, and velocity) and determines a point-wise estimate of yield production as a function of area (e.g. bushels per acre). The measurement system 130 determines yields at a particular interval (e.g. each second) and, thereby, can determine yields as a set of discrete measurements across a field.

In some cases, measured indicators may be erroneous. That is, a measurement system 130 may inaccurately measure and/or quantify agricultural field production (i.e., yield). For example, in a case where the measurement system 130 is a combine harvester, grain flow sensors responsible for measuring grain flow into the harvester used to determine field yield are generating inaccurate quantifications of yield. In particular, the grain flow sensors are producing erroneous measured indicators at the beginning and end of harvesting passes in the agricultural field and, subsequently, any yield map generated by the yield model would include inaccurate yield values.

Accordingly, a measurement system 130 (or network system 120, or yield model 112) may filter (i.e., remove) the erroneous measured indicators before using the indicators to generate a yield map. Various criteria can be used to filter erroneous measurement indicators.

In one example, indicators measured by the measurement system 130 during specific times may be filtered. For example, measured indicators obtained during a period of time after a measurement system begins measuring yield may be filtered (i.e., start pass delay). Similarly, measured indicators obtained during a period of time before the measurement system stops measuring yield may be filtered (i.e., end pass delay). The periods of time may be predetermined (e.g., 12 s), selected by an operator of the client system (e.g., as an input), etc.

In one example, measured indicators that exceed the biological limit for yield may be filtered. That is, for a given soil type and/or climatic zone, a certain crop may have a biological limit to its yield. For example, in Western Canada, the biological limit for feed barley is, approximately, 196 bushels/acre. As such, measured indicators exceeding those values may be filtered. Here, the biological limits may be accessed from the network system 120 via the network 150 or may be stored locally on the measurement system 130.

In one example, measured indicators that exceed localized difference thresholds may be filtered. That is, some variation in yield across a field is common; abrupt variation is less common unless an external influence (e.g., flooding, chemical drift, or wildlife damage) is introduced. Thus, if a single measured indicator lies outside a threshold amount from the distribution of its local neighbor measured indicators, the outlier may be filtered. The thresholds may be predetermined (e.g., 25% variation), selected by an operator of the client system (e.g., as an input), etc.

In various environments, measured indicators obtained by a measurement system 130 can include, for example, up to fifty percent erroneous measured indicators. As such, appropriately filtering measured indictors is important to accurately generating a yield map using a yield model.

An observation system 140 is any system or device that can provide observed indicators to the network system and client system. Observed indicators are any type of spatial agricultural datasets or observations describing observed characteristics of the agricultural field. For example, observed indicators may be imagery indicators, weather indicators, or soil indicators. In some examples, an observation system 140 is a system observing some aspect of the field and storing the observation for later quantification. For example, an observation system 140 may be an observation satellite that captures images of an agricultural field as the satellite passes over the field. The measurement system can be many other systems. For example, the image may be captured by a drone or an aircraft rather than a satellite.

Imagery indicators are obtained as multiband or single band e imagery, such as, for example, images, spectral maps, etc. Imagery indicators can be obtained from observation systems such as, for example, satellites, drones, and airplanes. Imagery indicators can play a heavy role in crop monitoring and forecasting. Additionally, vegetation indices may be determined from imagery indicators. These indicators correlate strongly with biomass in certain crop types and, thereby, can be a strong indicator of crop yield. Further, the indicators can also correlate to nitrogen content and other physical parameters (e.g., pigment concentrations).

Weather indicators are obtained as climate-pertinent variables, such as, for example, min/max temperature, relative humidity, precipitation, wind speed/direction, etc. Weather indicators can be event-based (e.g. the maximum temperature for the day) or aggregate (e.g. the accumulated rainfall over the month of June or during a particular stage in a crop's life cycle). Weather indicators can be obtained from observation systems such as, for example, weather measurement stations, historical weather databases, etc. Weather indicators can be a strong indicator of crop yield.

Soil indicators are obtained as static and dynamic characteristics of soil and can include, for example, soil texture, water-holding capacity, topography, and climate zone. Soil indicators can also have dynamic properties such as, for example, pre-season and in-season measurement of macronutrients (e.g. nitrogen), micronutrients (e.g. boron), and other properties (e.g. pH, electrical conductivity, etc.). Soil indicators can be obtained from observation systems such as, for example, a soil sampling and testing system. Soil indicators can be a strong indicator of yield.

Of course, other observed indicators are possible. Any variable that can be designated spatially may be considered as an observed indicator. Other observed indicators can include, for example, equipment types, irrigation parameters, crop varieties, genetics, seed population per acre, row spacing, nitrogen availability, maturity ratings, fertilizer/insecticide application, and seeding and application dates.

III. Generating a Yield map

A client system 110 uses a yield predication model 112 to generate a yield map for an agricultural field. The yield model 112 receives a location (or some other identifier) of the agricultural field as input and provides a yield map as an output. When generating a yield map, the yield model 112 may request, and receive, indicators from the network system 120 to facilitate generating the yield map. Network system 120 may access measured indicators from a measurement system 130 and observed indicators from an observation system 140, respectively, to generate a yield map for the agricultural field.

Figure 2:
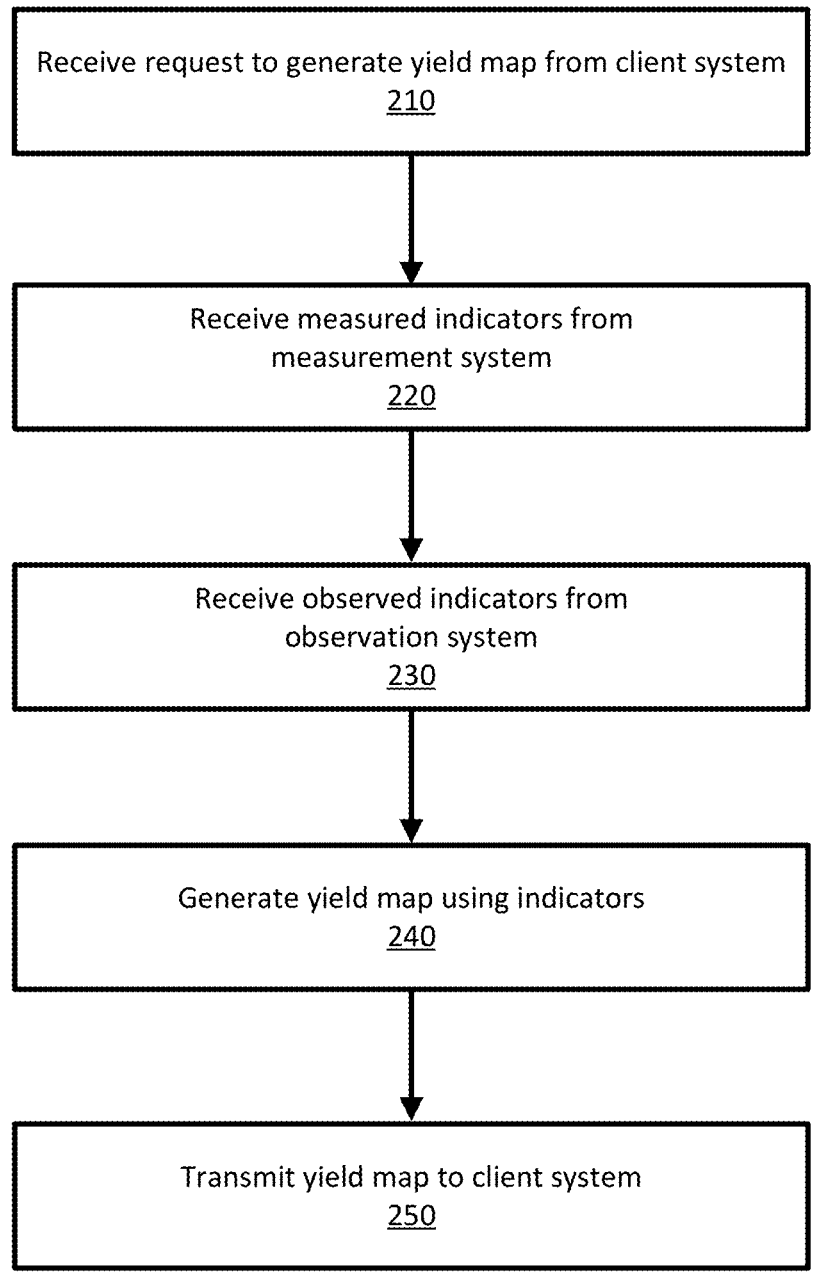
FIG. 2 is a flow diagram illustrating an example method for generating a yield map, according to one example embodiment.

FIG. 2 illustrates a flow diagram of a method 200 for generating a yield map. The method 200 may be executed by a yield model 112 executing on client system 110. In various embodiments, the method 200 can include additional or fewer steps and the steps may occur in any order.

To begin, a yield model 112 receives 210 a request to generate a yield map for an agricultural field. In this example, an operator of the client system 110 inputs a location of the agricultural field (e.g., coordinates) into the yield model 112 and initializes the request. The yield model 112 accesses a map (or some other spatial representation) of the agricultural field using the coordinates. Here, the operator manages the agricultural field and is a person responsible for crop production in the agricultural field.

The yield production model 112 receives 220 measurement indicators from a measurement system 130 operating in the field. In this example, the measurement system 130 is a combine harvester and the measurement indicators are quantifications of a crop yield as the combine harvester travels through the field.

The yield model 112 receives 230 observed indicators from an observation system 140 that has previously observed the field. In this example, the observation system 140 is a satellite and the observed indicator is a satellite image of the field. Additionally, the yield model 112 receives observed indicators that are a dataset indicating the pre-season soil nitrogen values obtained from an observation system 140 that is a soil fertilizing machine. In some configurations an observed indicator may be an indicator observed concurrently to a measured indicator. For example, a combine harvester may capture images of the field as it harvests plants.

The yield model 112 generates 240 a yield map using the indicators. In this example, the yield map is a field raster indicating a determined yield and/or a measured yield for areas in the field based on the satellite image, the nitrogen dataset, and the measured yield values. The yield map is configured for display as a heat map on the client system 110 such that the operator can easily visualize different areas and regions of determined yield.

The yield model 112 transmits 250 the yield map to the client system 110. The operator of the client system may read the yield map and take action in the agricultural field to enhance yield. For example, the operator may change how the combine harvester travels through the field to increase yield values. In some examples, the yield map is transmitted to the measurement system 130 as it travels through that field.

IV. Applying a Yield Model

Figure 3:
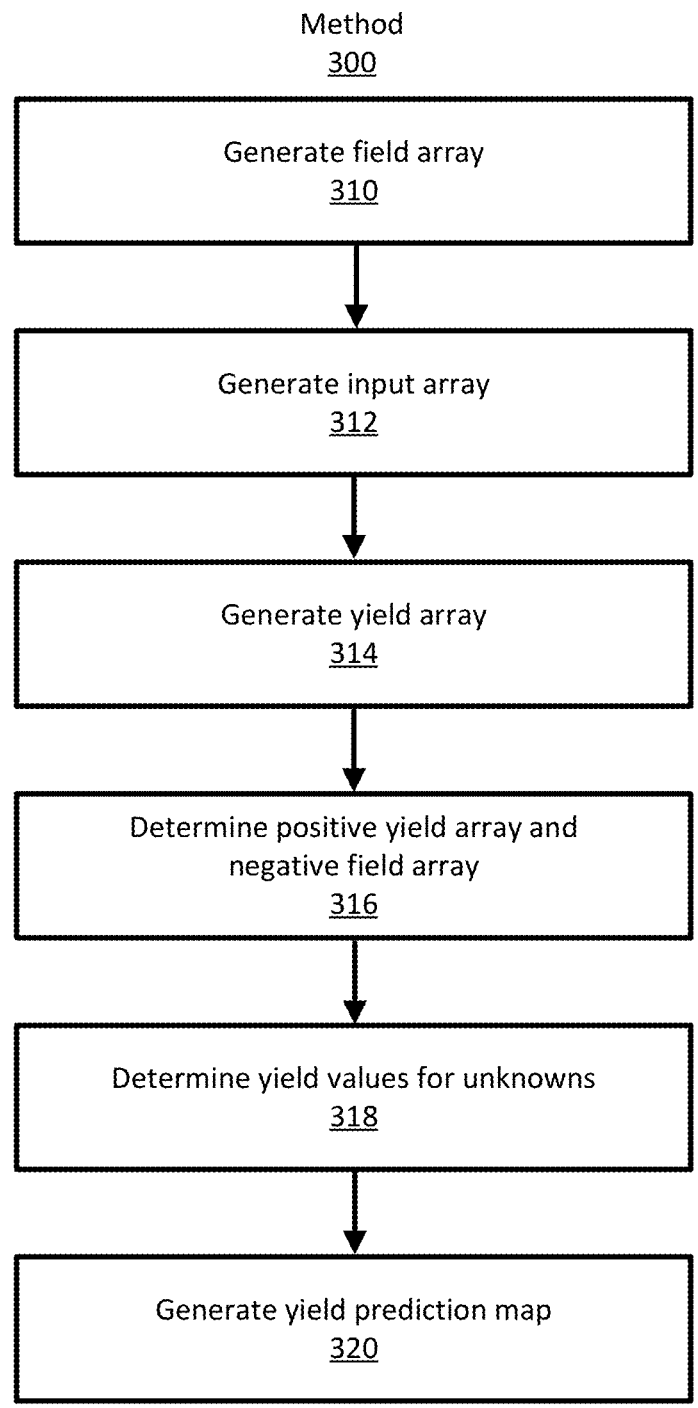
FIG. 3 illustrates a flow diagram of a method yield model executes to generate a yield map using observed indicators and measured indicators, according to one example embodiment.

FIG. 3 illustrates a flowchart of a method 300 that yield model 112 executes to generate a yield map using observed indicators and measured indicators. The method 300 may be executed by a yield model 112 executing on a client system 110. The method 300 will be described in reference to FIGS. 4-8. In various embodiments, the method 300 can include additional or fewer steps and the steps may occur in any order.

To begin, yield model 112 generates 310 an array representing the agricultural field ("field array"). That is, the yield model 112 generates a data structure representing a spatial layout of the agricultural field. In one example the field array can be represented as:

$$G=\{g_1, g_2, \ldots, g_n\} \quad (1)$$

where G is the field array and $g_i$ is a cell in the field array G. Each cell $g_i$ in the field array G represents a real world area in the agricultural field such that the field array G, in aggregate, represents the entire agricultural field. For example, the yield model 112 may partition a map of an agricultural field (i.e., field array G) into smaller map areas (i.e., cells g). In various examples, the configuration of a field array G (e.g., array size, cell size, cell shape, etc.) may be predetermined (e.g., each cell is a 1 m$^2$ square), defined by an operator of client system 110 (e.g., as an input), or any other method of defining the field array G or cells g in a field array G.

Yield estimation model 112 generates 312 an array from any number of observed indicators ("input array"). That is, the yield model 112 generates 312 a data structure representing the spatial layout of observed indicators describing the agricultural field. The input array can be represented as:

$$X=\{x_1, x_2, \ldots, x_n\} \quad (2)$$

where X is the input array and $x_i$ is a value, or values, of an observed indicator ("input"). For example, an input $x_i$ may be a satellite image taken of a field before flowering, the accumulated rainfall for the amount of June, or may be any other input that may be spatially resolved. More generally, each input $x_i$ in the input array X corresponds to an observed indicator input into the yield model 122.

Yield model 112 spatially interpolates each of the inputs $x_i$ in an input array X across the field array G representing the agricultural field. That is, for every cell $g_i$ in field array G, i.e., $g_i \in G$, yield model 112 maps that cell $g_i$ to an input $x_i$ of the input array X Therefore, each input x of the input array X is spatially resolved according to the cells g of the field array G.

The method for mapping a cell $g_i$ to an input $x_i$ in an input array X depends on the type of information encoded in the input $x_i$. For example, if the input $x_i$ is a set of points (e.g. soil cores), the yield model 112 may apply a kriging interpolation method to map the grid cells g to input $x_i$. Other similar interpolation methods may be appropriate. In another example, if the input $x_i$ is an array of values (e.g., pixels in a satellite image), yield model 112 may apply a set of morphological operators (e.g. warping, subsampling, supersampling, etc.) to align the array of the input $x_i$ to the cells g of the field array G.

An input $x_i$ mapped to the cells g of a field array G is a mapped input $x_{i,m}$ and an input array X whose inputs $x_i$ are all mapped inputs $x_m$ is a mapped input array $X_m$. In some cases, depending on the interpolation method, mapped inputs $x_m$ may include missing values ("null values"). That is, when mapping a cell $g_i$ to an input $x_i$ the yield model 112 did not return an interpolated value for that cell $g_i$. Null values in mapped input arrays $X_m$ allow utilization of observation indicators with missing or incomplete data. For example, an input $x_i$ that is a satellite image including clouds, which obstruct a part of the agricultural field, may have null values when mapped to the field array G.

Figure 4A:
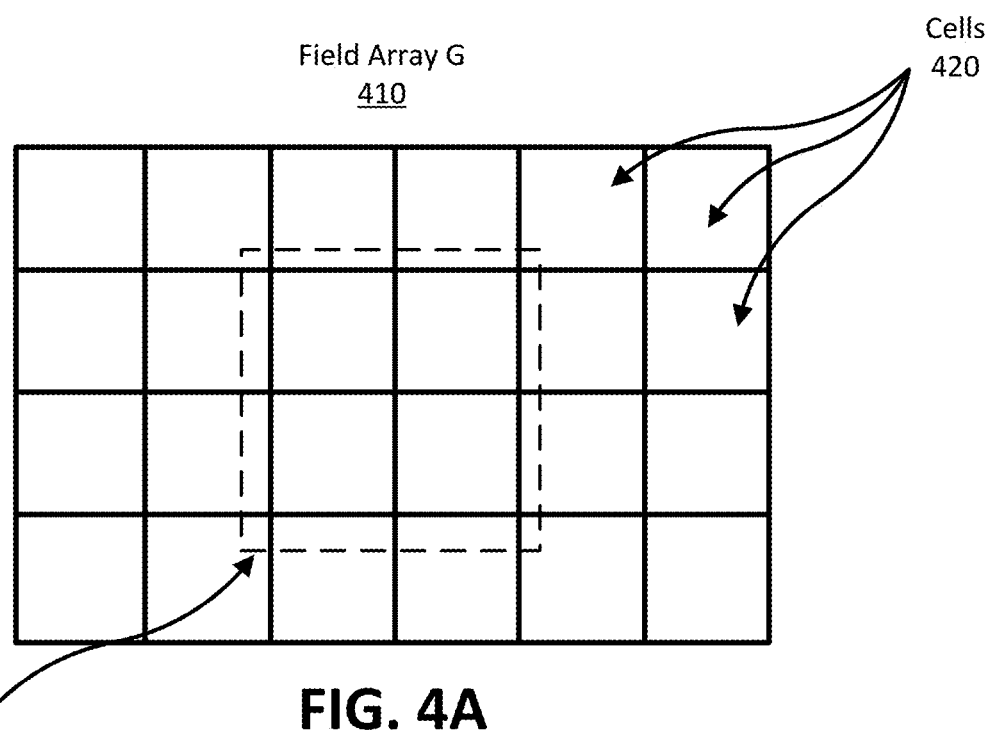
FIG. 4A is an illustration of a field array, according to one example embodiment.
Figure 4B:
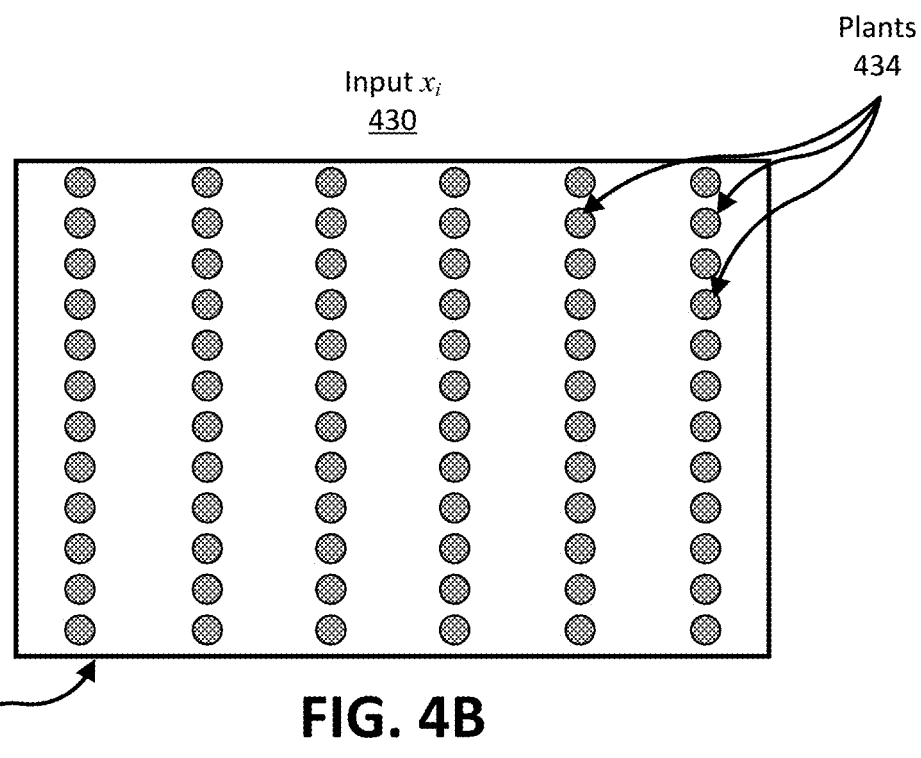
FIG. 4B is an illustration of an input that is a satellite image, according to one example embodiment.
Figure 4C:
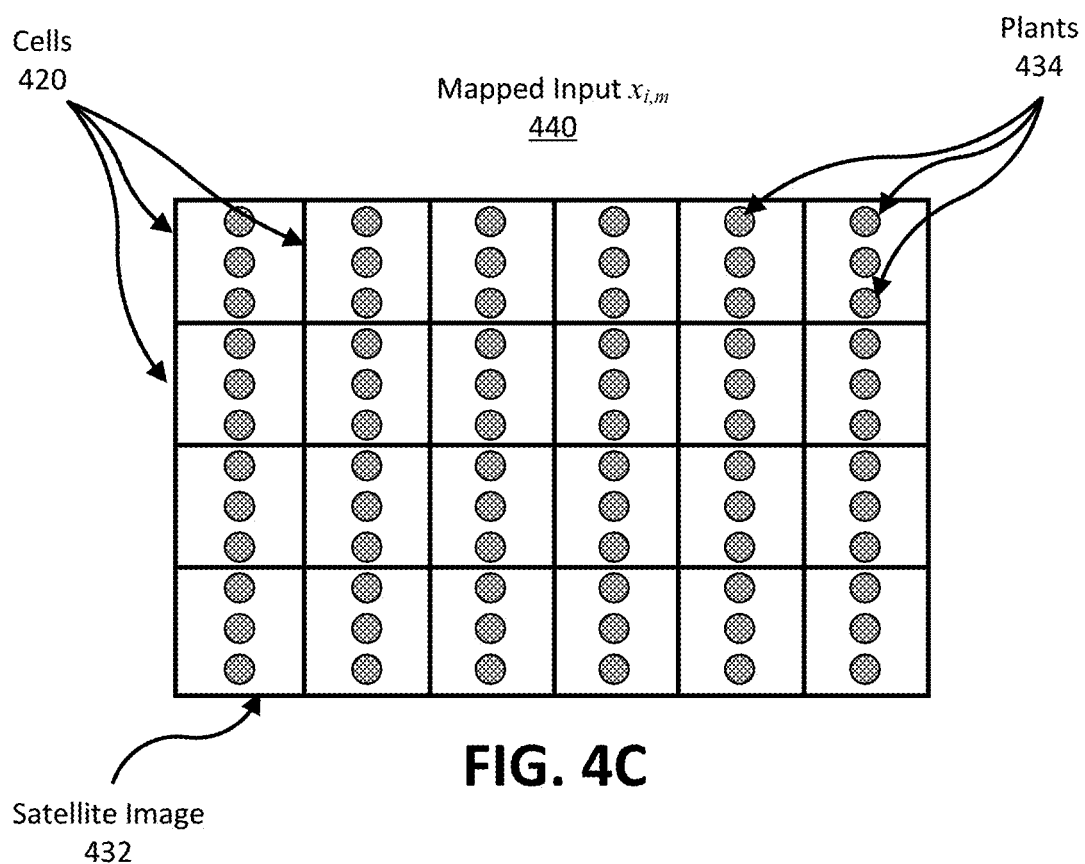
FIG. 4C is an illustration of a mapped input, according to one example embodiment.

FIGS. 4A-4C illustrate the process of yield model 112 mapping cells g of a field array G to an input $x_i$ in an input array X. FIG. 4A illustrates a field array G 410 including a number of cells g 420. Each cell $g_i$ 420 is illustrated as a small square and the field array G 410 is the combination of all the small squares. The cells g 420 of the field array G 410, in aggregate, approximate the size and shape of the agricultural field for which the yield model 112 is generating a yield map. FIG. 4B illustrates an input $x_i$ 430 from the input array X. Here, the input $x_i$ 430 is a satellite image 432 of the agricultural field including a number of plants 434. The boundary of the agricultural field is illustrated as a black line and the plants 434 are illustrated as patterned circles. FIG. 4C illustrates a mapped input $x_{i,m}$ 440 of a mapped input array $X_m$. Here, the cells g 420 of the field array G 410 in FIG. 4A have been mapped to the input $x_i$ 430 of FIG. 4B. The mapped input $x_{i,m}$ 440 is illustrated as the satellite image 432 overlaid with the cells 420 of the field array G 410. In subsequent figures (e.g., FIGS. 5A-7), for clarity, all illustrated cells correspond to the four centermost cells 422 of the field array G 410 shown in FIG. 4A. The four centermost cells 422 are outlined by a dashed line.

Figure 5A:
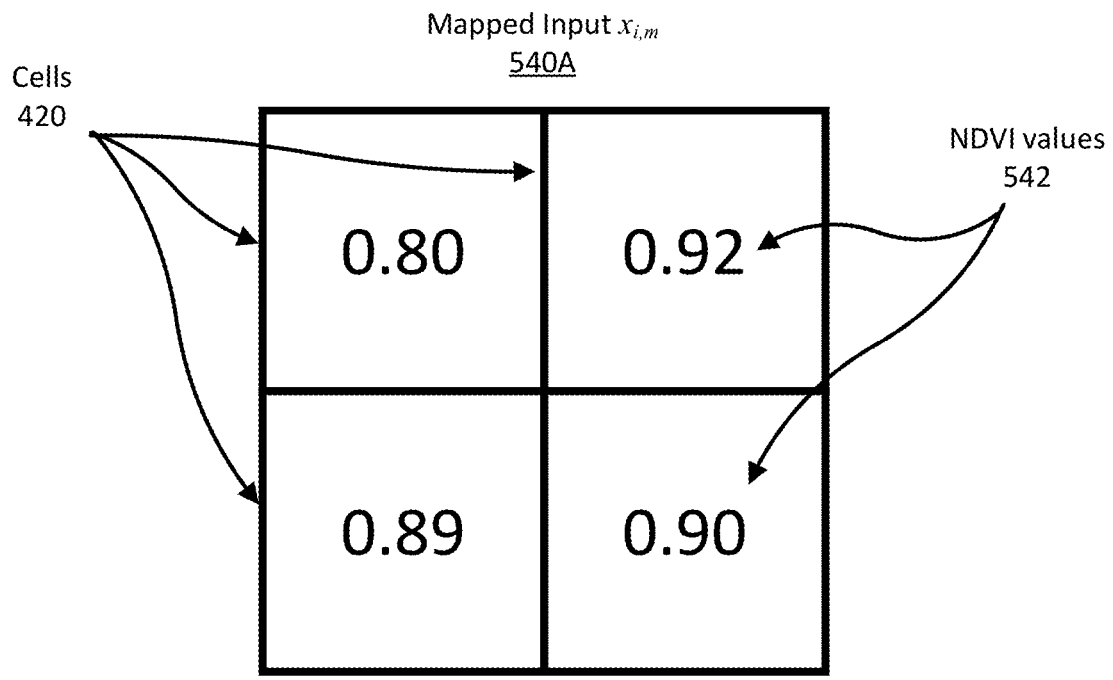
FIG. 5A-5B are illustrations of mapped inputs, according to some example embodiments.
Figure 5B:
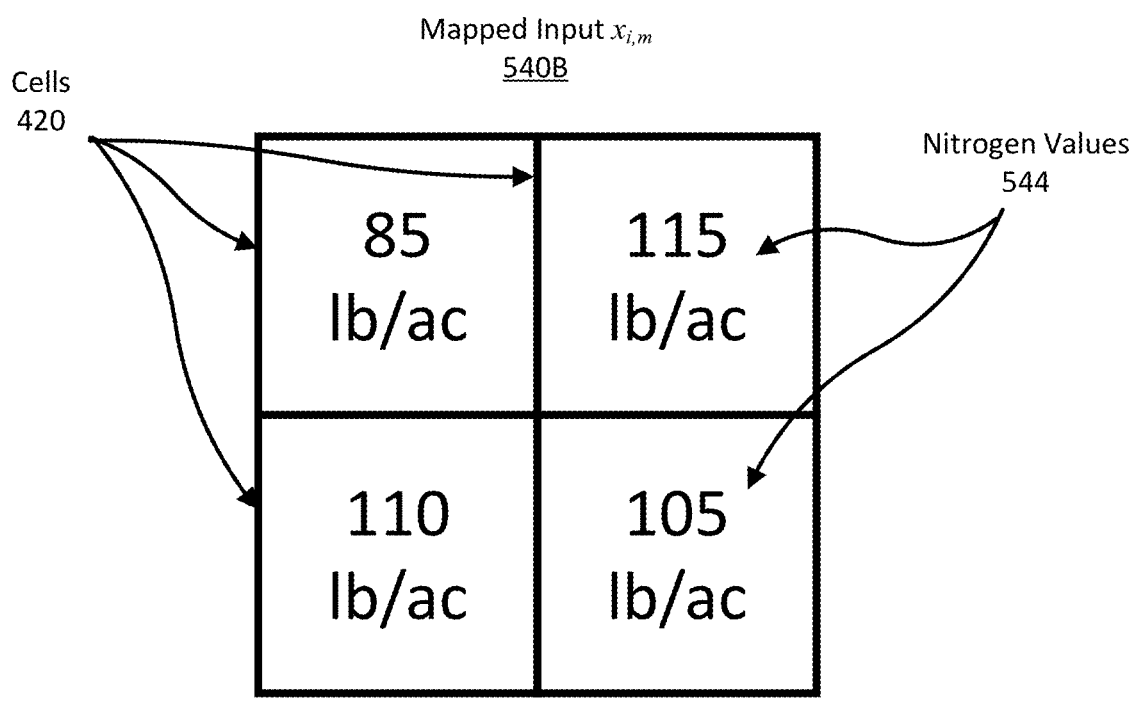

FIGS. 5A-5B illustrate other examples of mapped inputs $x_m$ from a mapped array $X_m$. FIG. 5A illustrates a mapped input $x_{i,m}$ 540A indicating the normalized difference vegetation index (NDVI) value 542 of each cell 420. That is, each cell 420 represents the NDVI value 542 for an area of the agricultural field. Here, the area is the real-world area associated with the corresponding cell g 420 in the field array G 410. In this example, the input $x_i$ 430 was a satellite image (e.g., satellite image 432). The yield model 112 calculates the NDVI value 542 of each pixel (or groups of pixels) in the satellite image 432. The yield model 112 then maps the NDVI values 542 to the cells 420 of the field array G 410 to generate a mapped input $x_{i,m}$ 540A of the NDVI values 542. Notably, the NDVI values from groups of pixels are combined into a single cell 420. FIG. 5B illustrates a mapped input $x_{i,m}$ 540B indicating the pre-season nitrogen values 544 (in lb./ac) for each cell 420. That is, each cell 420 represents the pre-season nitrogen values 544 for the soil in an area of the agricultural field. In this example, the input $x_i$ 430 was an array of soil nitrogen levels observed in the agricultural field before the current agricultural season. Each nitrogen level in the array corresponds to a particular location (or area) in the agricultural field. The yield model 112 maps the nitrogen levels to the cells 420 of the field array G 410 to generate a mapped input $x_{i,m}$ 440 of preseason nitrogen values 544. While the examples in FIGS. 5A and 5B are NDVI and pre-season nitrogen values, any other observed indicator may be used to Yield model 112 generates 314 an array from measured indicators ("yield array"). That is, the yield model 112 generates a data structure representing the spatial layout of measured indicators in the agricultural field. Generally, the measured indicators are high-confidence measured indicators because they have been filtered as previously described. However, yield model 112 may receive unfiltered measured indicators and filter the indicators before generating a yield array. The yield array can be represented as $$Y=\{y_1, y_2, \ldots, y_n\} \quad (3)$$

where Y is the yield array and $y_i$ is a value, or values, of a measured indicator ("yield points"). Each yield point $y_i$ is associated with the location in the field in which it was measured. Here, the yield points y are a quantification of crop yield measured by a combine harvester at a location in the agricultural field.

Yield model 112 maps the yield points y in the yield array Y to the cells g of the field array G to generate a mapped yield array $Y_m$. That is, for every cell $g_i$ in field array G, i.e., $g_i \in G$, yield model 112 maps that cell $g_i$ to yield points y of the yield array Y. In this manner, each cell in a mapped yield array $Y_m$ may indicate a quantification of crop yield in the area of the agricultural field associated with that cell $g_i$.

Yield model 112 generates a mapped yield array $Y_m$ according to a yield mapping function F. The yield mapping function F is a function that maps yield points y as a yield value to a cell $g_i$ of the field array G to generate the mapped yield array $Y_m$. The mapping occurs according to a criteria that defines whether a cell g in a field array G qualifies for the mapping.

By way of illustration, a yield mapping function F has a criteria for mapping yield points y to a cell g of the field array G to generate a mapped yield array $Y_m$. The criteria defines that, for a region of the agricultural field associated with a particular cell $g_i$ of a field array G, the corresponding cell in the mapped yield array $Y_m$ has a yield value if that cell includes at least one yield point y. That is, a cell of a mapped yield array $Y_m$ has a yield value if the region of the agricultural field represented by that cell includes at least one yield point. Additionally, here, for each cell of a mapped yield array $Y_m$, the yield mapping function F creates a yield value for the cell that is the average value of all yield points y within that cell. That is, a yield value for a cell in a mapped yield array $Y_m$ is an average of all yield points measured within the corresponding region of the field.

Other criteria for a yield mapping function F generating a mapped yield array are possible. For example, yield model 112 may map values to cells of the yield array whose Euclidean distance from a measured point is below a set threshold. Further, other functions for generating a yield value for a cell of a mapped yield array are possible. For example, a yield mapping function F may determine a yield value by calculating a median instead of a mean, or interpolating from yield points y within and outside of the cell.

Figure 6A:
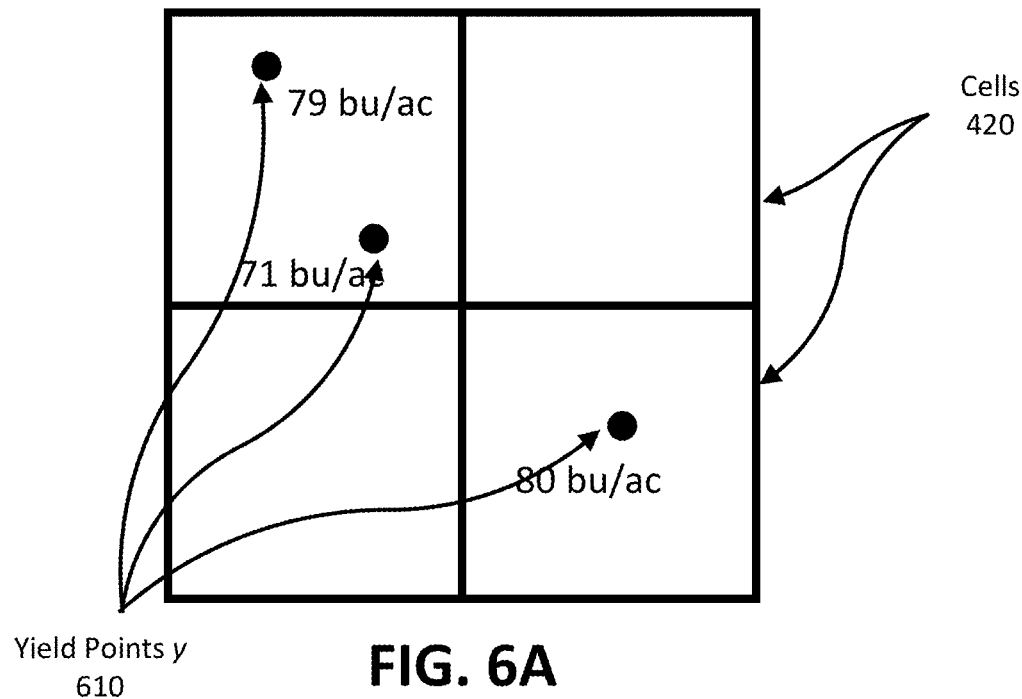
FIG. 6A is an illustration of yield points located in their corresponding cells of a field array, according to one example embodiment.
Figure 6B:
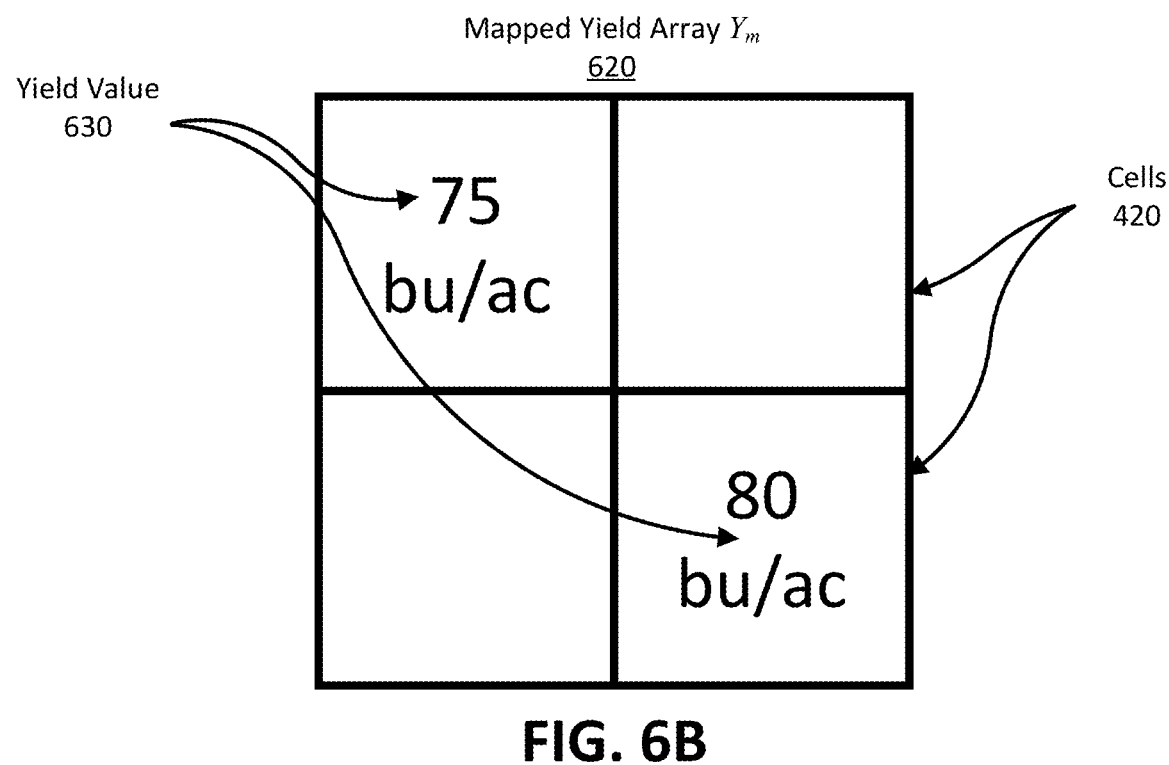
FIG. 6B is an illustration of a mapped yield array, according to one example embodiment.

FIGS. 6A and 6B illustrate an example of generating a mapped yield array from yield points. FIG. 6A illustrates a number of yield points 610, each of which corresponds to a measurement location in the agricultural field. Each yield point y 610 is illustrated as a dot and corresponds to a measured indicator from the field (e.g., a measurement of yield in bushels/acre). For clarity, the yield points 610 are illustrated within the cells 420 of a field array G 410 at locations corresponding to their measurement locations. That is, all of the yield points 610 within a particular cell 420 were measured in a region of the field that corresponds to the region of the field represented by that cell 420. Notably, there are no yield points in the upper right and lower left cells.

FIG. 6B illustrates a mapped yield array. A similar yield mapping function F, as previously described, maps the yield points y 610 to cells 420 in a mapped yield array $Y_m$ 620. That is, here, the top left cell and bottom right cell each have a yield value 630 because that cell includes at least one yield point y 610. The top right and bottom left cells are null values because there are no yield points y located within those cells. The yield value 630 of the top left cell is the average of the two yield points 610 in that cell. Correspondingly, the yield value of the bottom right cell is the value of the single yield point in that cell.

As previously described, measured indicators may be erroneous and, thereby, the density of yield points y in a yield array Y may be low. Depending on the density of the yield points y in a yield array Y, and the density of cells g in the field array G, some cells of the mapped yield array may $Y_m$ may include yield values while others include null values (as seen in FIG. 6B). That is, a mapped yield array $Y_m$ is an array of cells including yield values ("positive yield array" $Y^+$) and an array of cells including null values ("negative yield array" $Y^-$). Accordingly, yield generation model 112 can determine 316 a negative yield array $Y^-$ and a positive yield array $Y^+$. Referring to the mapped yield array $Y_m$ of FIG. 6B, the positive yield array $Y^+$ includes the top left and bottom right cells and the negative yield array $Y^-$ includes the bottom left and top right cells.

The yield model 112 creates an array of data P ("predictor array") using the mapped input array $X_m$ and the positive yield array $Y^+$. A predictor array P is defined as:

$$P = \{p_1, p_2, \ldots, p_n\} \quad (4)$$

where P is the predictor array and $p_i$ are the values corresponding to spatially equivalent cells in the mapped input array $X_m$ and positive mapped yield array $Y^+$ ("predictors"). More explicitly, the value of each predictor $p_i$ are all the values in the spatially equivalent cell from all of the mapped inputs $x_m$ in the mapped input array $X_m$ and the yield value from the same cell in the positive yield array $Y^+$. The predictor array P represents, in aggregate, a dataset that can be used for supervised learning where the predictor array is an input and yield values are an output.

Referring again to FIG. 6B, the top left cell and the bottom right cell are included in the positive yield array $Y^+$. Thus, a predictor array P has a predictor $p_i$ corresponding to the top left cell and a predictor $p_i$ corresponding to the bottom right cell. Referring also to mapped inputs $x_m$ in FIG. 5A and FIG. 5B, the predictor p for the top cell is $p_i = [0.80, 85, 75]$ and the predictor p for the bottom right cell is $p_i = [0.90, 105, 80]$.

Similarly, the yield model creates an array of data U ("unknown array") using the mapped input array $X_m$ and the negative yield array $Y^-$. An unknown array U is defined as:

$$U = \{u_1, u_2, \ldots, u_n\} \quad (5)$$

where U is the unknown array and $u_i$ are the values corresponding to similar cells in the mapped input array $X_m$ and the negative mapped array $Y^-$. More explicitly, the values of each unknown $u_i$ are all the values in the same cell from all of the mapped inputs $x_m$ in the mapped input array $X_m$ and the null value from the same cell in the negative yield array.

Referring again to FIG. 6B, the bottom left cell and the top right cell are included in the negative mapped array $Y^-$. Thus, an unknown array U has an unknown u corresponding to the top left cell and an unknown u corresponding to the top right cell. Referring also to mapped inputs $x_m$ in FIG. 5A and FIG. 5B, the unknown u for the bottom left cell is $u_i = [0.89, 110, \text{null}]$ and the unknown u for the top right cell is $u_i = [0.92, 115, \text{null}]$.

Yield model 112 determines yield values for each null value in each unknown u in unknown array U using the predictor array P. More explicitly, yield model 112 inputs a predictor array P and outputs a yield value for each cell of an unknown array. That is, yield model 112 determines yield values for cells in the mapped yield array that did not include yield points. Thus, the null value for each unknown u in an unknown array U is assigned a predicted yield value determined by the yield model 112.

In various embodiments, yield model 112 can use any standard classification and/or regression methods to determine 318 yield values for the unknown array U. In some examples, client system 110 generates and/or continuously updates functions used by the yield model 112 to determine 318 yield values using the predictor arrays P. The yield model 112 can include any method or methods that maps a set of predictors p (i.e., input values) in a predictor array P to a yield value. Some example models using classification and/or regression methods include feature selection, over-fit control, validation through training, and test sets would be performed. The yield model 112 may also output a set of variables used by the yield model 112 in determining yield values. Additionally, the yield model may also output a list of evaluation metrics from training the yield model using predictor arrays P. The metrics may include accuracy, precision, F1 score, etc. The metrics can be used to determine whether a sufficiently accurate model has been generated.

The yield model 112 combines the known yield values included in the predictor array P and the determined yield values in the unknown array U to generate 320 a yield map. Each cell of the yield map includes either a measured yield value (from the predictor p) or a determined yield value (from the unknown u).

Figure 7:
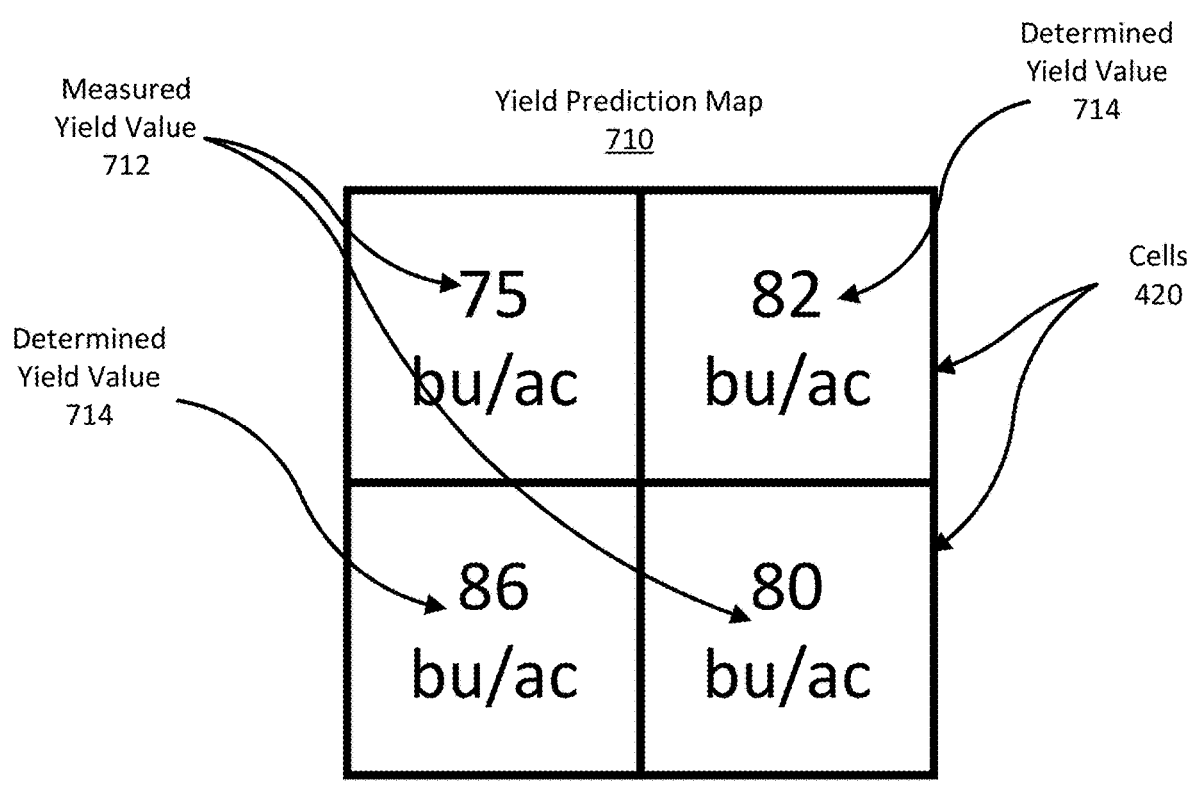
FIG. 7 is an illustration of a yield map, according to one example embodiment.
Figure 8:
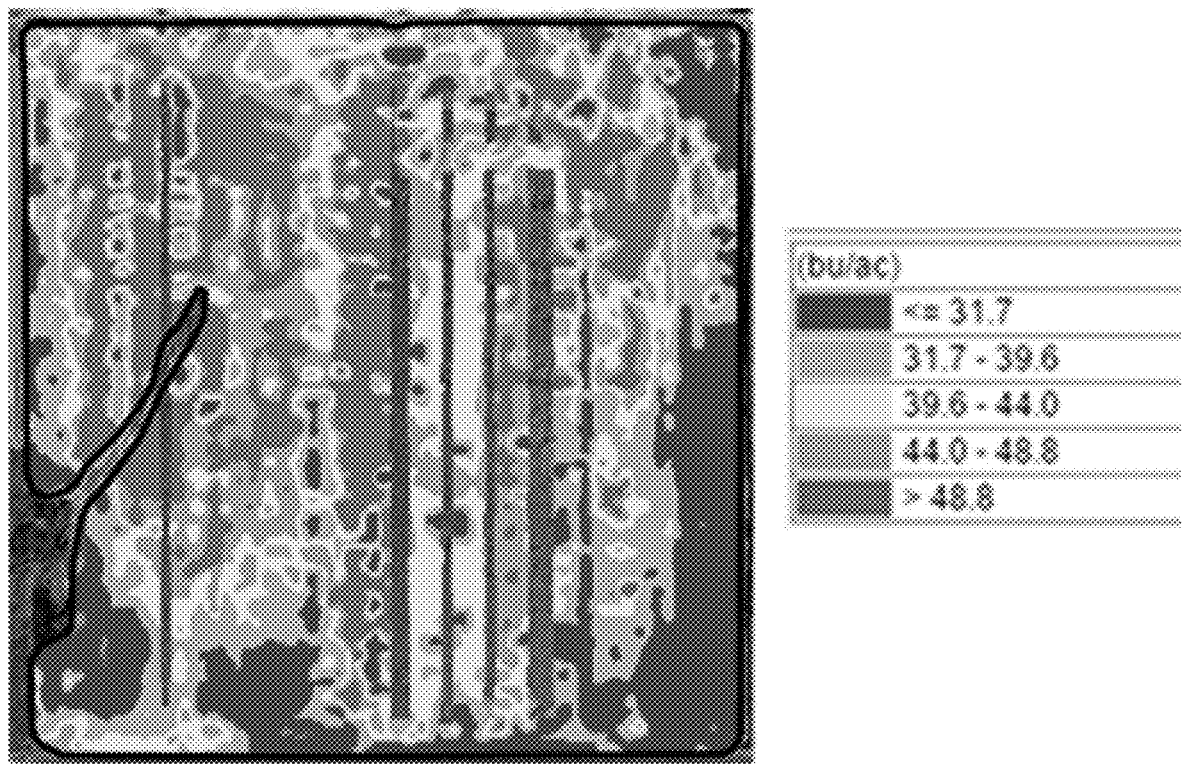
FIG. 8 is an example visualization generated from a yield map according to one example embodiment.

FIG. 7 illustrates a yield map including both measured yield values and/or determined yield values. Here, the yield map 710 includes measured yield values in the top left and bottom right cells. The measured yield values 712 are the yield values from the corresponding cells in the predictor array P. Additionally, the yield map 710 includes determined yield values 714 in the bottom left and top right cells. The determined yield values 714 are the yield values determined for an unknown u in the unknown array U by the yield model 112. Each of the determined yield values 714 are in cells corresponding to the null values for which they were determined.

The yield model 112 may generate a visualization of the yield map. For example, the yield model may generate a heat map using the values in the yield map. The yield model 112 may overlay the heat map on an image of the agricultural field for which the yield model 112 is determining yield values. For example, FIG. 9 is a visualization of a yield map. Here, the visualization 810 is a heat map overlaid on a satellite image of the agricultural field for which the yield model determined yield values. Each color in the visualization represents a range of yield values. Additionally, each cell in a yield map is associated with a region of the agricultural field and, thereby, the color for each pixel of the visualization corresponds to a yield value. The yield map presents data included in a yield map in such a way that operators can more easily make determinations about agricultural field management.

V. Additional Model Functionality

Additionally, yield model can generate yield values using temporally defined data. For example, an indicator may be obtained from different growing seasons. As such, predictors in the predictor array may reflect temporally different agricultural data. In this case, the yield model can determine yield values for unknowns in the unknown array by leveraging agricultural data from previous seasons. Similarly, yield model 112 can update functions for determining yield values that allow mapping temporally different data to yield values.

The yield model 112 can generate a yield map using only observed indicators. In this case, yield model 112 can access indicators (measured and/or observed) from a previous season and assign them as observed indicators. Yield model 112 inputs indicators from previous seasons and one or more observed indicators from the current season. Yield model generates a yield map using only the indicators from the previous season and the observed indicators from the current season. Thus, yield model 112 can generate a yield map without measured indicators from the current season.

VI. Additional Configuration Considerations

Likewise, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Upon reading this disclosure, those of skill in the art will appreciate still additional alternative structural and functional designs as disclosed from the principles herein. Thus, while particular embodiments and applications have been illustrated and described, it is to be understood that the disclosed embodiments are not limited to the precise construction and components disclosed herein. Various modifications, changes, and variations, which will be apparent to those skilled in the art, may be made in the arrangement, operation, and details of the method and apparatus disclosed herein without departing from the spirit and scope defined in the appended claims.

What is claimed is:

1. A method for generating a yield map for an agricultural field, the method comprising:
  receiving a request from an operator to generate a yield map for the agricultural field;
  generating a field array including a plurality of cells, each cell corresponding to an area in the agricultural field;
  generating an input array including a plurality of inputs, each input in the array describing an observed condition of the agricultural field, and each input having a plurality of cells corresponding to the cells in the field array;
  generating a yield array including a plurality of cells, each cell of the yield array having yield value measured at a location in the agricultural field, and each cell in the yield array corresponding to a cell in the field array;
  generating a yield map including a plurality of cells from the yield array, the yield map including a first subset and second subset of cells, each cell in the yield map having a yield value or a null value,
    yield values assigned to the first subset of cells, where each cell in the subset cells corresponds to a cell in the yield array including a yield value, the yield value in the yield map the yield value in the corresponding cell of the yield array, and
    null values assigned to the second subset of cells;
  for each cell in the yield map having a null value,
    generating a yield value for the cell using a yield model, the yield model determining a yield value for the cell using conditions of the agricultural field described in the inputs of the input array for that cell; and transmitting the yield map to the operator.

2. The method of claim 1, wherein generating the field array further comprises:
partitioning a map of the agricultural field into a field array.

3. The method of claim 1, wherein generating an input array further comprises:
mapping the plurality of cells in a field array to each input of the input array such that each input of the input array includes a plurality of cells corresponding to an area in the agricultural field.

4. The method of claim 1, wherein generating a yield array further comprises:
mapping the plurality of cells in a field array to the yield array such that the yield array includes a plurality of cells corresponding to an area in the agricultural field.

5. The method of claim 1, wherein the yield value of a cell in a yield array is a function of the yield values measured at locations in the field corresponding to that cell of the yield array.

6. The method of claim 1, further comprising:
generating a visualization of the yield map.

7. The method of claim 1, wherein the yield values are measured by a yield measurement system operating in the agricultural field.

8. The method of claim 7, wherein the yield measurement system is in a combine harvester operating in the agricultural field.

9. The method of claim 1, wherein the inputs for the input array include any of an image, soil data, or vegetation index data.

10. The method of claim 1, further comprising:
filtering yield values measured at locations in the agricultural field that are erroneous.

11. A system comprising one or more processors and one or more memories storing computer program instructions for generating a yield map for an agricultural field, the instructions when executed by the one or more processors to perform the steps including:
receiving a request from an operator to generate a yield map for the agricultural field;
generating a field array including a plurality of cells, each cell corresponding to an area in the agricultural field;
generating an input array including a plurality of inputs, each input in the array describing an observed condition of the agricultural field, and each input having a plurality of cells corresponding to the cells in the field array;
generating a yield array including a plurality of cells, each cell of the yield array having yield value measured at a location in the agricultural field, and each cell in the yield array corresponding to a cell in the field array;
generating a yield map including a plurality of cells from the yield array, the yield map including a first subset and second subset of cells, each cell in the yield map having a yield value or a null value,
yield values assigned to the first subset of cells, where each cell in the subset cells corresponds to a cell in the yield array including a yield value, the yield value in the yield map the yield value in the corresponding cell of the yield array, and null values assigned to the second subset of cells;
for each cell in the yield map having a null value,
generating a yield value for the cell using a yield model, the yield model determining a yield value for the cell using conditions of the agricultural field described in the inputs of the input array for that cell; and transmitting the yield map to the operator.

12. The system of claim 11, wherein the instructions, when executed by the one or more processors, further perform steps including:
partitioning a map of the agricultural field into a field array.

13. The system of claim 11, wherein the instructions, when executed by the one or more processors, further perform steps including:
mapping the plurality of cells in a field array to each input of the input array such that each input of the input array includes a plurality of cells corresponding to an area in the agricultural field.

14. The system of claim 11, wherein the instructions, when executed by the one or more processors, further perform steps including:
mapping the plurality of cells in a field array to the yield array such that the yield array includes a plurality of cells corresponding to an area in the agricultural field.

15. The system of claim 11, wherein the yield value of a cell in a yield array is a function of the yield values measured at locations in the field corresponding to that cell of the yield array.

16. The system of claim 11, wherein the instructions, when executed by the one or more processors:
generating a visualization of the yield map.

17. The system of claim 11, wherein the yield values are measured by a combine harvester operating in the agricultural field.

18. The method of claim 1, wherein the inputs for the input array include any of an image, soil data, or vegetation index data.

19. The method of claim 1, further comprising:
filtering yield values measured at locations in the agricultural field that are erroneous.

20. A method for generating a yield map for an agricultural field, the method comprising:
generating an input array including a plurality of cells, each cell of the input array corresponding to an observed indicator describing a condition of an agricultural field;
generating a yield array including a plurality of cells, each cell of the yield array corresponding to a measured indicator describing a yield value measured at a location in the agricultural field;
generating a yield map including a plurality of cells, each cell having a yield value from its corresponding cell in the yield array or a null value when there is no yield value in the corresponding cell in the yield array; and
for each cell in the yield map having a null value,
generating a yield value for the cell using a yield model, the yield model determining a yield value for the cell using conditions of the agricultural field described in the input array for that cell.

* * * * *